(12) United States Patent
Nishio et al.

(10) Patent No.: US 9,764,119 B2
(45) Date of Patent: Sep. 19, 2017

(54) URETHRAL STRICTURE TREATMENT APPARATUS AND URETHRAL STRICTURE TREATMENT METHOD

(71) Applicant: TERUMO KABUSHIKI KAISHA, Tokyo (JP)

(72) Inventors: Kosuke Nishio, Machida (JP); Riyaheh S. Hazama, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 70 days.

(21) Appl. No.: 14/858,489

(22) Filed: Sep. 18, 2015

(65) Prior Publication Data
US 2016/0089522 A1 Mar. 31, 2016

(30) Foreign Application Priority Data

Sep. 30, 2014 (JP) ................................. 2014-201608

(51) Int. Cl.
| | |
|---|---|
| *A61F 2/04* | (2013.01) |
| *A61M 27/00* | (2006.01) |
| *A61B 17/00* | (2006.01) |
| *A61M 29/00* | (2006.01) |
| *A61M 31/00* | (2006.01) |

(Continued)

(52) U.S. Cl.
CPC ..... *A61M 27/008* (2013.01); *A61B 17/00234* (2013.01); *A61M 25/04* (2013.01); *A61M 25/1011* (2013.01); *A61M 29/00* (2013.01); *A61M 29/02* (2013.01); *A61M 31/00* (2013.01); *A61B 2017/00292* (2013.01); *A61M 2025/0175* (2013.01); *A61M 2025/1013* (2013.01); *A61M 2210/167* (2013.01)

(58) Field of Classification Search
CPC ........ A61F 2/04; A61M 29/00; A61M 27/008
USPC .............................................. 623/23.66, 23.77
See application file for complete search history.

(56) References Cited

U.S. PATENT DOCUMENTS 5,588,965 A * 12/1996 Burton ............... A61M 25/1011
604/101.05
8,679,147 B2 * 3/2014 Isham .................... A61B 5/411
606/197

(Continued)

FOREIGN PATENT DOCUMENTS

| JP | 10-506038 A | 6/1998 |
|---|---|---|
| WO | WO 96/27406 A1 | 9/1996 |

*Primary Examiner* — Suzette J Gherbi
(74) *Attorney, Agent, or Firm* — Buchanan Ingersoll & Rooney PC

(57) ABSTRACT

A urethral stricture treatment apparatus and treatment method are disclosed, which can easily inhibit the position of a medical material from deviating from a treatment site and can make the medical material selectively indwell different treatment sites. The urethral stricture treatment apparatus can have a dilation portion, which dilates in a state of holding a medical material providing an epithelial function so as to bring the medical material into contact with an inner wall of urethra, and a restriction portion which is provided in a position closer to a distal side than the dilation portion in an insertion direction such that a distance between the restriction portion and the dilation portion can be relative changed, and comes into contact with external urethral sphincter in a living body so as to restrict the movement of the medical material toward the distal side.

15 Claims, 19 Drawing Sheets

(51) Int. Cl.
*A61M 25/04* (2006.01)
*A61M 25/10* (2013.01)
*A61M 29/02* (2006.01)
*A61M 25/01* (2006.01)

(56) References Cited

U.S. PATENT DOCUMENTS

| | | | | |
|---|---|---|---|---|
| 2008/0140098 A1* | 6/2008 | Kumar | ............... | A61B 17/11 606/153 |
| 2009/0177288 A1* | 7/2009 | Wallsten | ............... | A61F 2/04 623/23.66 |
| 2010/0256608 A1* | 10/2010 | Bolmsjo | ............... | A61M 25/0017 604/544 |
| 2011/0208022 A1* | 8/2011 | Brawer | ............... | A61B 10/0045 600/309 |
| 2013/0345653 A1* | 12/2013 | Feneley | ............... | A61M 25/0017 604/328 |
| 2015/0216609 A1* | 8/2015 | Arastoo | ............... | A61B 17/320725 600/37 |
| 2015/0217100 A1* | 8/2015 | Karino | ............... | A61B 1/307 604/22 |
| 2015/0327980 A1* | 11/2015 | Nishio | ............... | A61F 2/0063 623/23.66 |
| 2015/0327982 A1* | 11/2015 | Nishio | ............... | A61M 25/0068 623/23.66 |
| 2016/0074186 A1* | 3/2016 | Sartor | ............... | A61M 25/0017 623/23.65 |
| 2016/0089169 A1* | 3/2016 | Nishio | ............... | A61F 2/04 606/194 |
| 2016/0135942 A1* | 5/2016 | Drager | ............... | A61F 2/0036 600/30 |
| 2016/0193469 A1* | 7/2016 | Cardinal | ............... | A61N 1/3605 607/46 |
| 2016/0213945 A1* | 7/2016 | Burwell | ............... | A61N 5/0601 |
| 2016/0242894 A1* | 8/2016 | Davis | ............... | A61F 2/90 |
| 2016/0243341 A1* | 8/2016 | Nishio | ............... | A61M 25/1011 |
| 2016/0346504 A1* | 12/2016 | Arora | ............... | A61B 5/6852 |

* cited by examiner

FIG. 11A
FIG. 11B
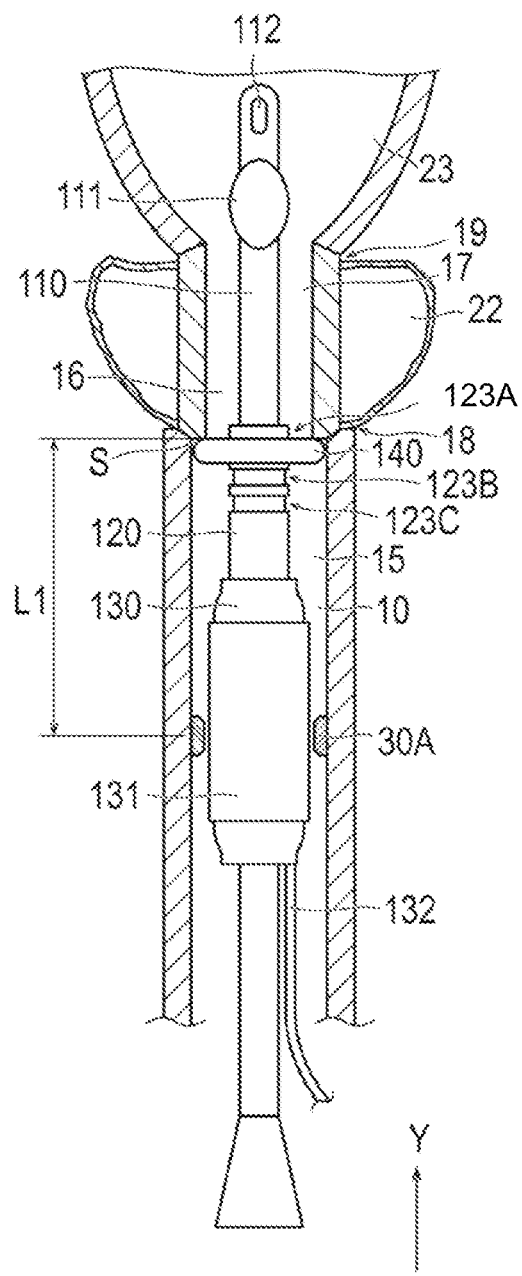
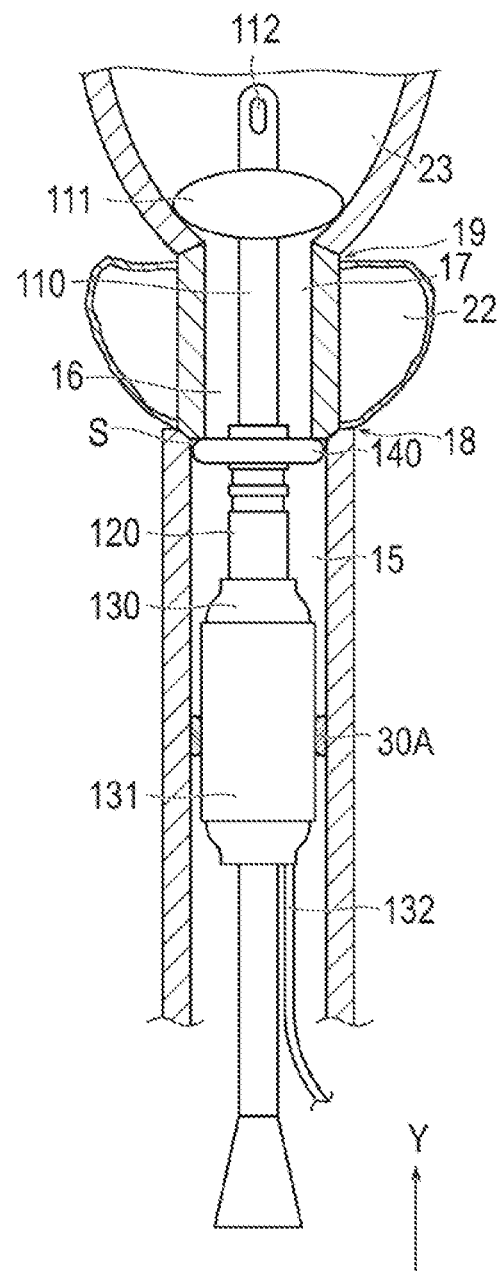

URETHRAL STRICTURE TREATMENT APPARATUS AND URETHRAL STRICTURE TREATMENT METHOD

CROSS-REFERENCES TO RELATED APPLICATIONS

This application claims priority to Japanese Application No. 2014-201608 filed on Sep. 30, 2014, the entire content of which is incorporated herein by reference.

TECHNICAL FIELD

The present disclosure generally relates to a urethral stricture treatment apparatus and a urethral stricture treatment method that are for treating urethral stricture.

BACKGROUND DISCUSSION

Urethral stricture is narrowing of the urethra that is a disease that can be caused by the following mechanism. When the urethral mucosa is wounded by injury or inflammation, the urethral mucosa or the corpus spongiosum penis surrounding the urethral mucosa develops into scar tissue in the process of wound healing, and as a result, the urethra can be narrowed due to the scar tissue.

A method of surgically reconstructing the urethra is known, in which to help prevent the recurrence of the urethral stricture, oral mucosa is grafted to a treatment site of the inner wall of the urethra by means of direct suture. However, this method can be relatively highly invasive to patients and can include a long period of hospitalization.

A method for treating urethral stricture is also known in which the prepuce of penis is held on the outer circumferential portion of a device, and the device is transurethrally inserted into the urethra in this state and brought into contact with a treatment site of the prepuce of penis so as to help prevent the recurrence of the urethral stricture.

As described in JP-A0-8-526731, a urethral catheter is disclosed that is transurethrally inserted into the urethra to help treat prostatic hypertrophy. According to the aforementioned document, in the urethral catheter, a balloon on the distal side is indwelled into the bladder, and a positioning balloon is disposed in the region of the bulb of penis, such that the urethral catheter can be fixed, and the urethral stricture caused by the prostatic hypertrophy can be treated as intended.

SUMMARY

However, in the case of treating the urethral stricture by the aforementioned method, because the position in which scar tissue is formed varies between patients, it can be difficult to adapt the device to an appropriate position in the treatment site.

A urethral stricture treatment apparatus is disclosed, which can easily inhibit the position of a medical material from deviating from a treatment site and can make the treatment material selectively indwell at different treatment sites, and a urethral stricture treatment method.

A urethral stricture treatment apparatus is disclosed for treating urethral stricture, the apparatus can include a dilation portion which dilates in a state of holding a medical material providing an epithelial function so as to bring the medical material into contact with an inner wall of the urethra; and a restriction portion which is provided in a position closer to a distal side than the dilation portion in an insertion direction such that a distance between the restriction portion and the dilation portion can be relatively changed, and comes into contact with external urethral sphincter in a living body so as to restrict the movement of the medical material toward the distal side.

According to an exemplary embodiment of the urethral stricture treatment apparatus, the urethral stricture treatment apparatus can further include a flexible and long main body portion which enables the dilation portion and the restriction portion to be fixed thereto and can be inserted into the urethra; and a distal side restriction portion which is provided in a position closer to the distal side than the restriction portion within the main body portion and comes into contact with internal urethral sphincter in the living body so as to restrict the movement of the medical material toward a proximal side in the insertion direction.

According to an exemplary embodiment of the urethral stricture treatment apparatus, the main body portion is constituted with a transparent or semitransparent member, and an insertion lumen into which an endoscope can be inserted is provided inside the main body portion.

According to an exemplary embodiment of the urethral stricture treatment apparatus, the dilation portion further has a holding member including a holding portion that can hold the restriction portion, and the restriction portion is a cyclic member which is fixed by being held in the holding portion.

According to an exemplary embodiment of the urethral stricture treatment apparatus, the apparatus further includes a fixing member provided with the restriction portion in the outer circumferential portion of the fixing member; and a fixing balloon which is provided in the inner circumferential portion of the fixing member and dilates in a circumferential direction so as to fix the fixing member and the main body portion.

According to an exemplary embodiment of the urethral stricture treatment apparatus, the dilation portion and the restriction portion are constituted so as to be able to move relative to each other in the insertion direction.

According to an exemplary embodiment of the urethral stricture treatment apparatus, the restriction portion is constituted so as to be able to be deformed by dilation.

According to an exemplary embodiment of the urethral stricture treatment apparatus, the restriction portion is a balloon.

A urethral stricture treatment method is disclosed for treating urethral stricture, the method including: an insertion step of inserting a urethral stricture treatment apparatus, which includes a dilation portion that can dilates in a state of holding a medical material providing an epithelial function, and a restriction portion that is disposed in a position closer to a distal side than the dilation portion and restricts the movement of the medical material toward the distal side in an insertion direction, into urethra; a contact step of bringing the restriction portion into contact with external urethral sphincter in a living body; an adjustment step of adjusting a distance between the dilation portion and the restriction portion; and a contact step of bringing the medical material into contact with a treatment site by dilating the dilation portion.

According to an exemplary embodiment of the urethral stricture treatment method, in the adjustment step, the distance between the dilation portion and the restriction portion is adjusted by moving the restriction portion relative to the dilation portion.

According to an exemplary embodiment of the urethral stricture treatment method, in the adjustment step, the distance between the dilation portion and the restriction portion is adjusted by moving the dilation portion relative to the restriction portion, in a state in which the restriction portion comes into contact with the external urethral sphincter.

According to an exemplary embodiment of the urethral stricture treatment apparatus, when the medical material is made to indwell at the treatment site, the restriction portion comes into contact with the external urethral sphincter in the living body, and as a result, the movement of the medical material toward the distal side is restricted. Accordingly, it is not necessary to use the technique of grafting the medical material and apparatus described above to the inner wall of the urethra by means of direct suture, and the position of the medical material can be relatively easily inhibited from deviating from the treatment site toward the distal side of the insertion direction. Furthermore, the restriction portion is provided such that a distance between the restriction portion and the dilation portion can be relatively changed. Consequently, the distance between the restriction portion and the dilation portion can be appropriately set according to the individual difference of the patient, and the medical material can selectively indwell at different treatment sites. Therefore, a urethral stricture treatment apparatus is disclosed, which can relatively easily inhibit the position of a medical material from deviating from a treatment site and can make the medical material selectively indwell at different treatment sites.

According to an exemplary embodiment of the urethral stricture treatment apparatus, in the main body portion which enables the dilation portion and the restriction portion to be fixed thereto, the distal side restriction portion is provided in a position closer to the distal side than the restriction portion. Therefore, when the medical material is made to indwell at the treatment site, the distal side restriction portion comes into contact with the internal urethral sphincter in the living body, and in this way, the movement of the medical material toward the proximal side is restricted. Consequently, the position of the medical material can be relatively easily inhibited from deviating from the treatment site toward the proximal side in the insertion direction.

According to an exemplary embodiment of the urethral stricture treatment apparatus, because an operator can perform an operation while observing the form of the urethra through an endoscope, the procedure becomes easier.

According to an exemplary embodiment of the urethral stricture treatment apparatus, the movement of the medical material toward the distal side in the insertion direction can be restricted by a simple structure.

According to an exemplary embodiment of the urethral stricture treatment apparatus, the fixing member and the main body portion can be reliably fixed by the fixing balloon.

According to an exemplary embodiment of the urethral stricture treatment apparatus, the dilation portion and the restriction portion are constituted such that they can move relative to each other in the insertion direction. Therefore, by appropriately moving the dilation portion or the restriction portion according to the individual difference of the patient, the medical material can selectively indwell at different treatment sites, and the operation becomes relatively easier.

According to an exemplary embodiment of the urethral stricture treatment apparatus, in a state in which the restriction portion has been contracted, the urethral stricture treatment apparatus can be inserted into the urethra. Therefore, the insertion of the apparatus becomes less invasive, and the strain imposed on the patient can be reduced.

According to an exemplary embodiment of the urethral stricture treatment apparatus, the movement of the medical material toward the distal side in the insertion direction can be inhibited by a simple structure.

According to an exemplary embodiment of the urethral stricture treatment apparatus, the position of the medical material can be relatively easily inhibited from deviating from the treatment site and to make the medical material selectively indwell at different treatment sites.

According to an exemplary embodiment of the urethral stricture treatment apparatus, by appropriately moving the restriction portion according to the individual difference of the patient, the medical material can selectively indwell at different treatment sites.

According to an exemplary embodiment of the urethral stricture treatment apparatus, by appropriately moving the dilation portion according to the individual difference of the patient, the medical material can selectively indwell at different treatment sites.

BRIEF DESCRIPTION OF THE DRAWINGS

FIG. 11A is a view for illustrating a procedure using the urethral stricture treatment apparatus according to the first exemplary embodiment.

FIG. 11B is another view for illustrating a procedure using the urethral stricture treatment apparatus according to the first exemplary embodiment.

DETAILED DESCRIPTION

Hereinafter, the embodiments of the present disclosure will be described with reference to drawings. In the following description, the dimensional ratios of the drawings are magnified for convenience and differ from the actual ratios in some cases. Furthermore, in the following description, within urethral stricture treatment apparatuses 1 and 2 according to the present embodiments, the side operated by a hand is called a "proximal side", and the side inserted into urethra 10 is called a "distal side".

The present disclosure described based on the following embodiments relates to a urethral stricture treatment apparatus for treating urethral stricture. For example, the present disclosure relates to a treatment apparatus which can inhibit the occurrence of restenosis (reocclusion) of the urethra after a treatment such as incision or the like is performed on a stenosed site formed in the urethra. First, the peripheral structure of the urethra of the living body, the mechanism causing the urethral stricture and restenosis, and the like will be described.

Figure 1A:
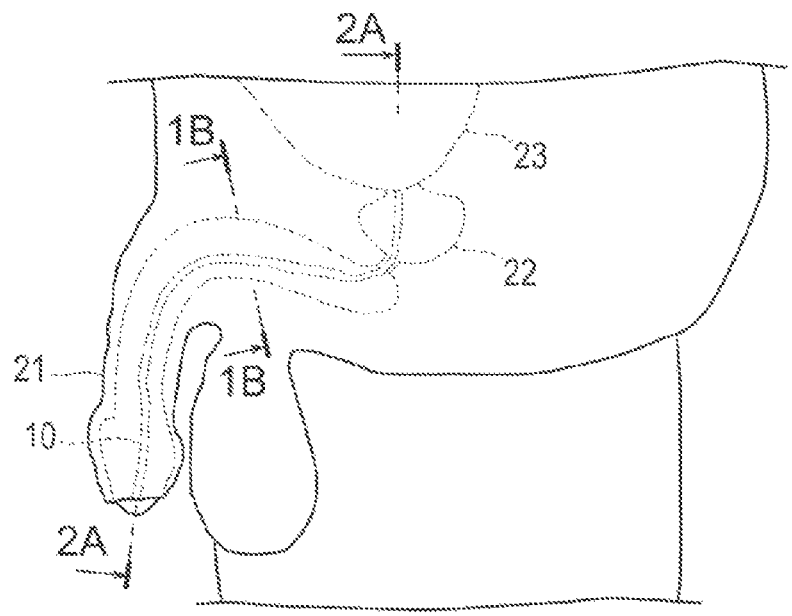
FIG. 1A is a view schematically showing a periphery of the urethra of a living body.
Figure 2:
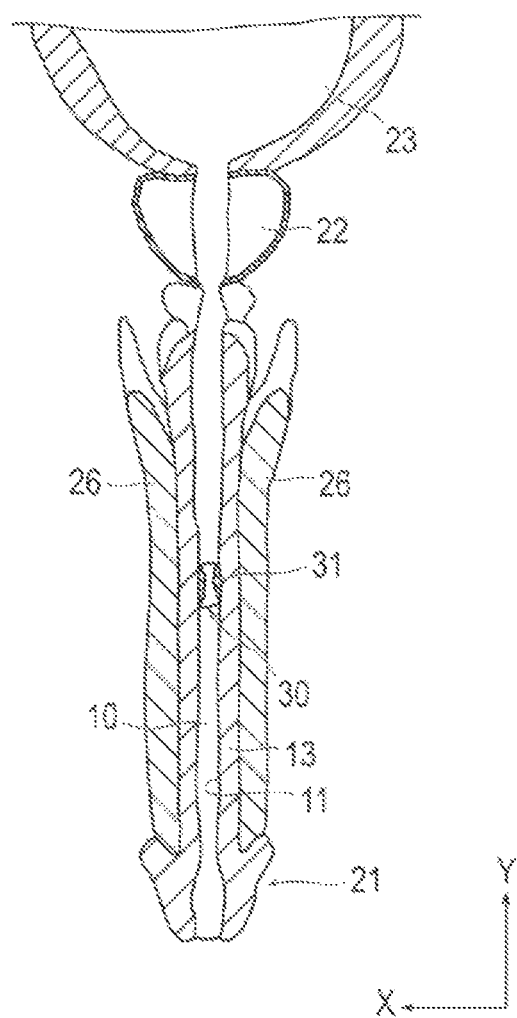
FIG. 2 is a sectional view of the urethra and the peripheral portion of the urethra shown in FIGS. 1A and 1B, which is taken along line 2A-2A (the line running along a direction in which the urethra extends) in FIG. 1A.
Figure 3A:
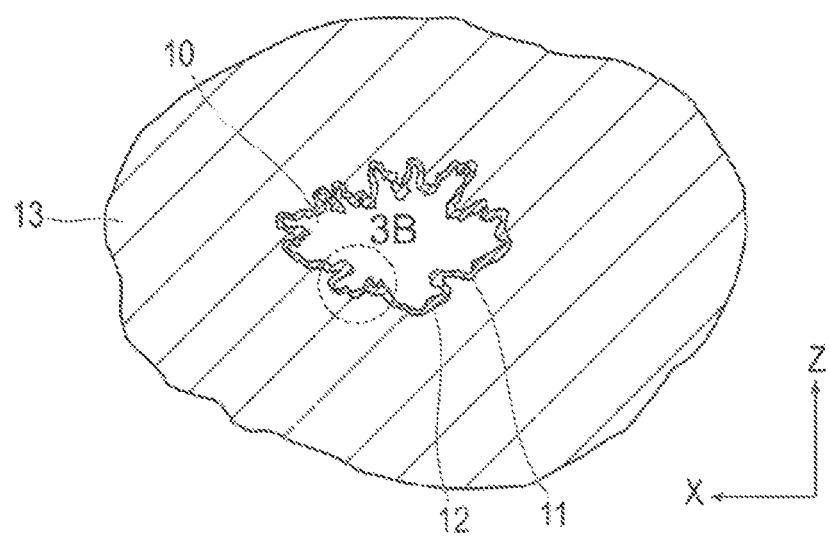
FIG. 3A is an enlarged cross-sectional view of the urethra and the corpus spongiosum penis showing the periphery of the urethra shown in FIG. 1B.
Figure 3B:
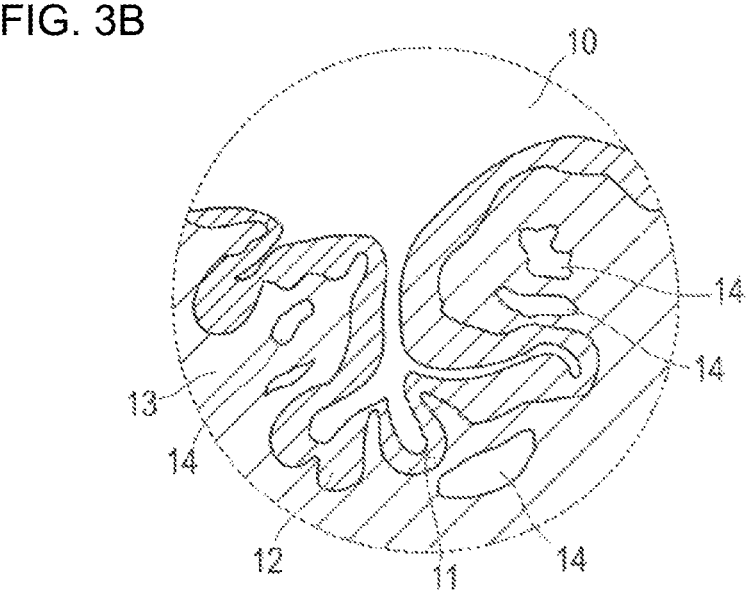
FIG. 3B is an enlarged sectional view of the portion indicated by the dotted line 3B shown in FIG. 3A.
Figure 4:
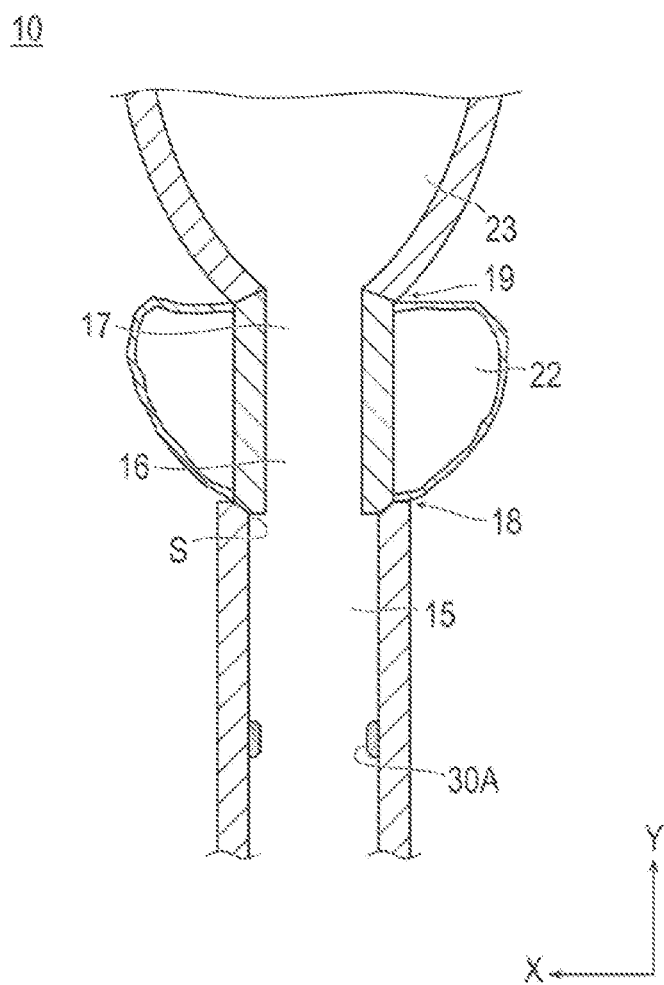
FIG. 4 is a schematic view showing the periphery of the urethra.
Figure 5:
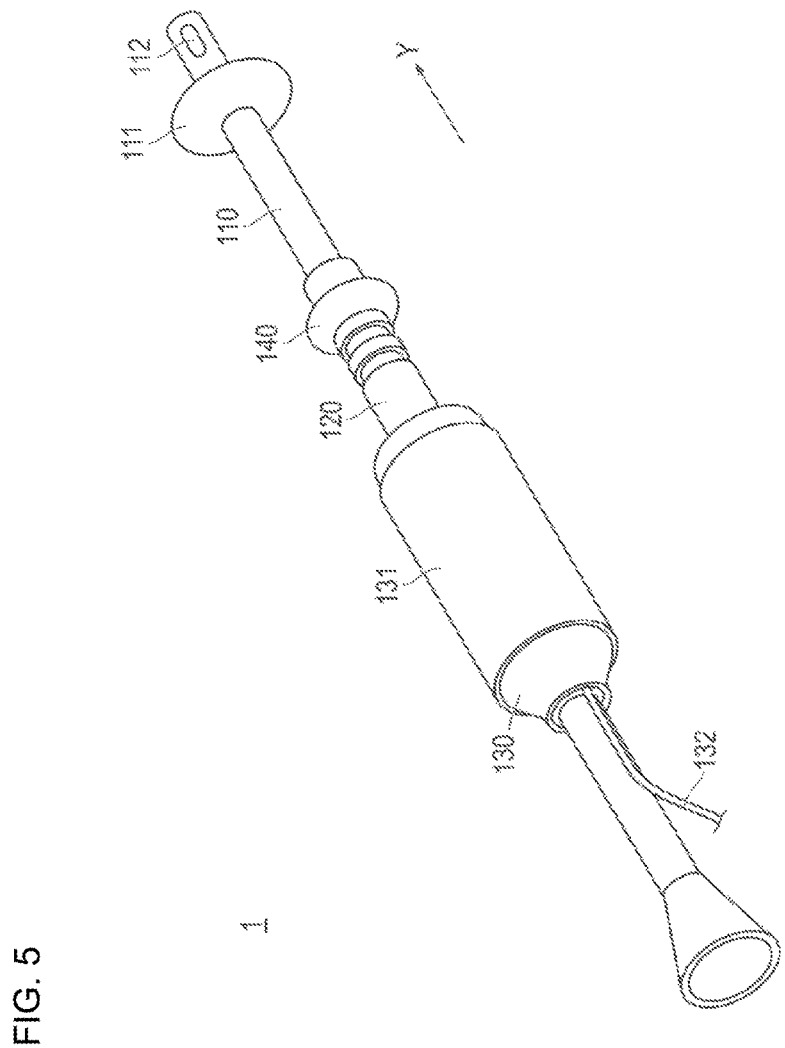
FIG. 5 is a perspective view showing a urethral stricture treatment apparatus according to a first exemplary embodiment of the present disclosure.
Figure 6:
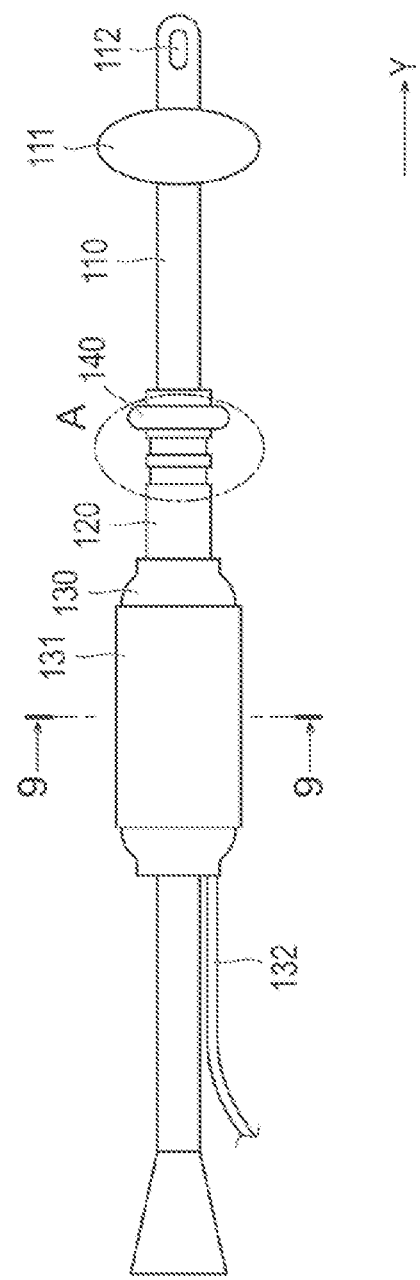
FIG. 6 is a plan view showing the urethral stricture treatment apparatus according to the first exemplary embodiment.

FIGS. 1A to 4 schematically show urethra 10 of a male and the peripheral portion thereof. As shown in FIG. 1A, the urethra 10 passes through the inside of penis 21 and the inside of prostate 22 and extends to bladder 23 in the lower abdomen of the living body. For example, as shown in FIG. 4, the urethra 10 includes bulbous urethra 15, a membranous portion 16 of the urethra, and prostatic urethra 17. Furthermore, external urethral sphincter 18 is in the vicinity of the boundary between the bulbous urethra 15 and the membranous portion 16 of the urethra. In addition, internal urethral sphincter 19 is in the vicinity of the boundary between the prostatic urethra 17 and the bladder 23. Moreover, a step S formed due to a difference of inner diameter is in the boundary between the bulbous urethra 15 and the membranous portion 16 of the urethra. The step S formed due to a difference of inner diameter occurs because the urethra 10 is closed by the external urethral sphincter 18.

Figure 1B:
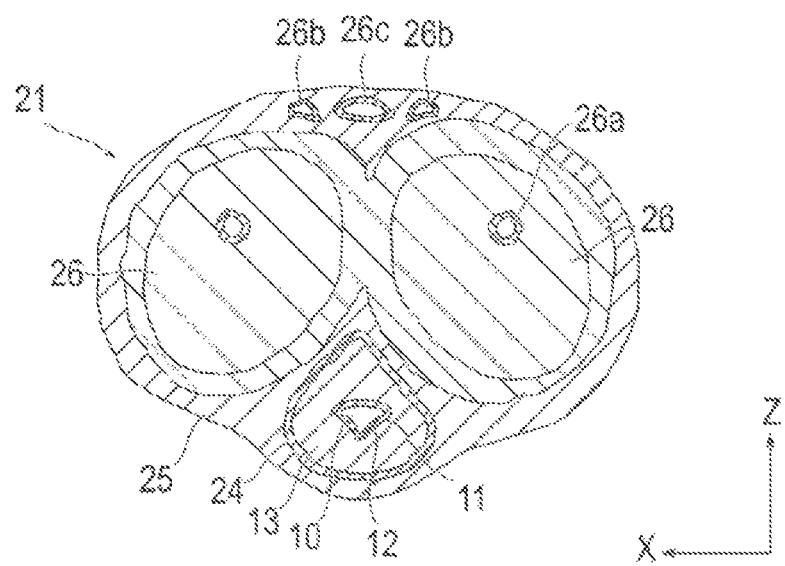
FIG. 1B is a cross-sectional view of the urethra taken along line 1B-1B shown in FIG. 1A.

As shown in FIGS. 1B and 3A, the urethra 10 has an inner wall 11 that is covered with urethral mucosa 12, and corpus spongiosum penis 13 is on the outside of the urethral mucosa 12. Furthermore, as shown in FIG. 3B, in the corpus spongiosum penis 13, there are blood vessels 14 called caverns of corpus spongiosum running in the form of a network. In each of the drawings, the X-axis indicates a width direction (horizontal direction of FIG. 1B) of the urethra, the Y-axis indicates a direction (vertical direction of FIG. 2) in which the urethra extends, and the Z-axis indicates a height direction (vertical direction of FIG. 1B) of the urethra.

As shown in FIG. 1B, the corpus spongiosum penis 13 is covered with tunica albuginae 24, and fascia 25 and corpus cavernosum penis 26 are on the outside the tunica albuginae 24. Atria profunda penis 26a is inside the corpus cavernosum penis 26, and atria dorsalis penis 26b and venae dorsalis penis 26c are above the corpus cavernosum penis 26.

The urethral stricture is a disease, which can be caused by the following mechanism. In the process in which the urethral mucosa 12 or the corpus spongiosum penis 13 is damaged by, for example, trauma or inflammation and then healed, the tissue of the urethral mucosa 12 or the tissue of the corpus spongiosum penis 13 surrounding the urethral mucosa 12 undergoes fibrosis or cicatrization. Consequently, a scar tissue 31 is formed in the inner wall 11 of the urethra as shown in FIG. 2, and as a result, the lumen of the urethra 10 is narrowed. In the urethra 10, the cross-sectional area of the site (stenosed site 30) at which the scar tissue 31 is formed becomes narrower than that of other sites of the urethra 10. Accordingly, urine does not easily pass through the site. When the urethral stricture occurs, the patient suffers from micturition disorders that can hinder smooth urination or cause complete urinary retention.

As a urethral stricture treatment method, for example, a method is tried in which a medical instrument such as a bougie (urethral dilator), a balloon, a cold knife, or a laser is transurethrally inserted into the urethra so as to treat the stenosed site, for example, by dilating the stenosed site or making an incision at the stenosed site by using the aforementioned medical instrument. Although the treatment method can bring about a temporary effect, the stenosed site 30 is formed again after the treatment is provided once, and therefore the urethral stricture can be likely to reoccur. Because the scar tissue 31 has liquid permeability, the periphery of the scar tissue 31 or the corpus spongiosum penis 13 under the scar tissue 31 is constantly exposed to liquid (for example, urine or blood) flowing in the urethra 10. Consequently, an inflammatory reaction is continuously induced, reconstruction of epithelial cells is hindered, and as a result, urethral stricture reoccurs.

Hereinafter, the constitution of the urethral stricture treatment apparatus according to the present disclosed will be described. The urethral stricture treatment apparatus according to the present disclosure is a treatment apparatus for making a medical material, which provides an epithelial function, indwell at a treatment site 30A (see FIG. 4) formed as a result of providing treatment such as incision or the like to the stenosed site 30 formed in the urethra 10. Herein, as the medical material, an epidermization sheet containing epithelial cells, such as an oral mucosa sheet, a sheet of prepuce of penis or the like, is used. The medical material can also include a collagen sheet seeded with epithelial cells and the like. Furthermore, the medical material can include a sheet, gel, and the like constituted with a biocompatible material that does not contain epithelial cells and has a function of preventing the infiltration of urine. In addition, the medical material can include a material that provides a factor or a stimulus accelerating the regeneration of the urethral mucosa. The form of the medical material is not limited to a sheet. The medical material may be in any form such as gel, liquid or the like, as long as it can indwell at a site to be treated.

Hereinafter, a urethral stricture treatment apparatus 1 according to a first embodiment of the present disclosure will be described. As shown in FIGS. 5 to 11B, the urethral stricture treatment apparatus 1 can include a balloon (dilation portion) 130 which dilated in a state of holding a medical material 131 providing an epithelial function so as to bring the medical material 131 into contact with the inner wall 11 of the urethra 10, and a restriction portion 140 which is disposed in a position closer to the distal side than the balloon 130 in the Y-direction (insertion direction) such that the distance between the restriction portion 140 and the balloon 130 can be relatively changed, and comes into contact with the external urethral sphincter 18 in the living body so as to restrict the movement of the medical material 131 toward the distal side in the Y-direction. Hereinafter, the constitution of the urethral stricture treatment apparatus 1 according to the first exemplary embodiment will be specifically described.

In the present specification, the "epithelial function" refers to a barrier function of preventing or reducing the contact between the corpus spongiosum penis 13 and liquid such as urine or the like as well as inflammatory components contained in the urethra 10. In the present exemplary embodiment, a sheet-like member composed of epithelial cells can be used as the medical material 131.

As shown in FIGS. 5 to 8, the urethral stricture treatment apparatus 1 according to the first embodiment has a urethral catheter (main body portion) 110, the balloon 130, the restriction portion 140, and a tubular member 150. The balloon 130 has an intermediate member (holding member) 120.

The urethral catheter 110 can be inserted into the urethra 10 and is flexible. As shown in FIGS. 5, 6, and 11A and 11B, the urethral catheter 110 has a distal side balloon (distal side restriction portion) 111 which is disposed in a position closer to the distal side than the restriction portion 140 in the Y-direction and comes into contact with the internal urethral sphincter 19 in the living body so as to restrict the movement of the medical material 131 toward the proximal side in the Y-direction, and a lumen (insertion lumen) 112 which is formed by making a hole penetrating the urethral catheter 110 in the Y-direction and enables urine or the like to pass through the lumen 112.

As will be described later, the balloon 130 and the restriction portion 140 can be fixed to the urethral catheter 110.

The urethral catheter 110 is constituted with a transparent or semitransparent resin material. According to this constitution, by inserting an endoscope into the lumen 112 at the time of a procedure, an operator can perform the procedure while observing the form of the urethra 10, and therefore the procedure becomes relatively easier. The urethral catheter 110 may not be a transparent member.

The distal side balloon 111 is constituted such that it can be deformed by dilation through a lumen, not shown in the drawing. The distal side balloon 111 is fixed to the outer circumferential portion of the urethral catheter 110 on the distal side of the urethral catheter 110 in the Y-direction. For example, the distal side balloon 111 is fixed to the urethral catheter 110 by means of bonding using an adhesive. However, the fixing method is not particularly limited, and welding or the like may be used.

Examples of the material constituting the urethral catheter 110 can include polymer materials, such as silicone rubber, latex rubber, polyolefin, crosslinked polyolefin, polyvinyl chloride, polyamide, a polyamide elastomer, polyester, a polyester elastomer, a polystyrene elastomer, polyurethane, a polyurethane elastomer, a fluororesin, polyimide and the like, and a mixture of these. Examples of the polyolefin include polyethylene, polypropylene, polybutene, an ethylene-propylene copolymer, an ethylene-vinyl acetate copolymer, an ionomer, and a mixture composed of two or more of these.

As the material constituting the distal side balloon 111, for example, a flexible material is preferable. Examples of such a material include a polymer material such as polyolefin, crosslinked polyolefin, polyester, a polyester elastomer, a polystyrene elastomer, polyvinyl chloride, polyurethane, a polyurethane elastomer, polyphenylene sulfide, polyamide, a polyamide elastomer, a fluororesin, silicone rubber, and latex rubber. The polyester is, for example, polyethylene terephthalate. The material constituting the distal side balloon 111 is not limited to the embodiment using the aforementioned polymer material alone. For example, a film obtained by appropriately laminating the aforementioned polymer materials on each other can be used.

Figure 7:
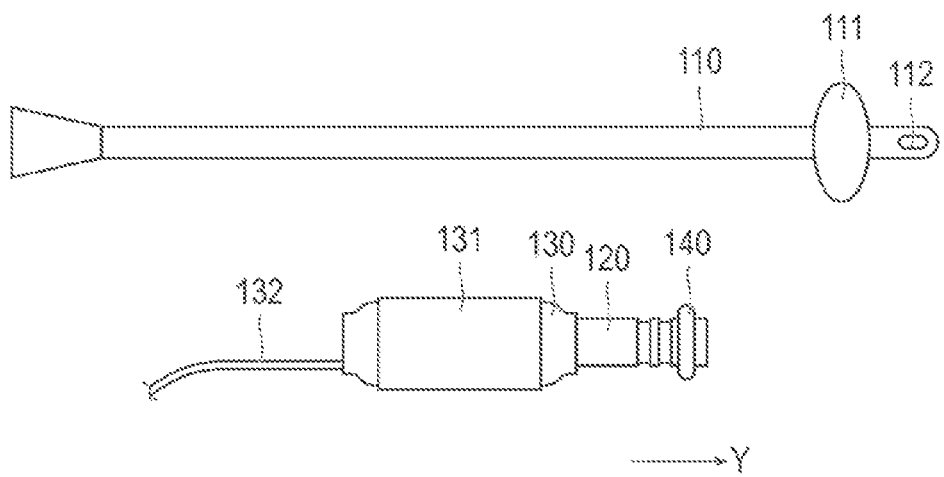
FIG. 7 is an exploded view showing the urethral stricture treatment apparatus according to the first exemplary embodiment.
Figure 8:
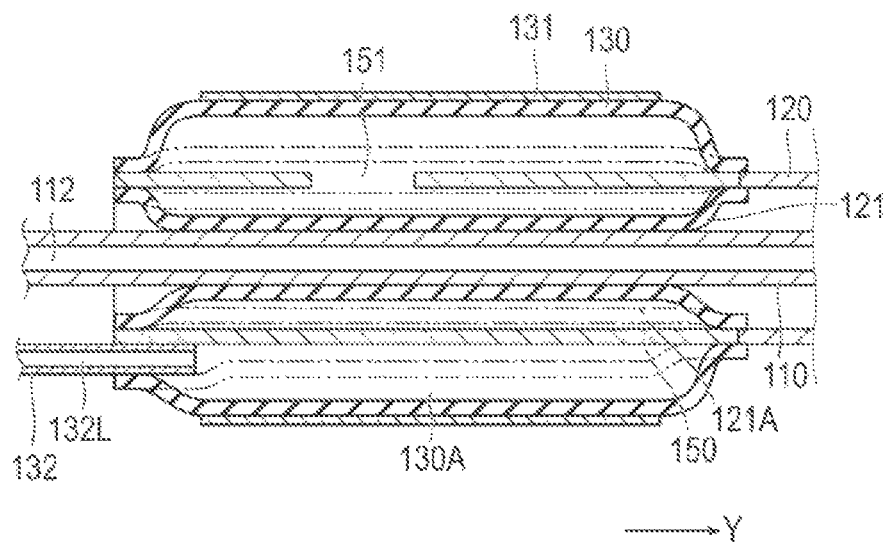
FIG. 8 is a front sectional view showing the vicinity of a balloon of the urethral stricture treatment apparatus according to the first exemplary embodiment.
Figure 9:
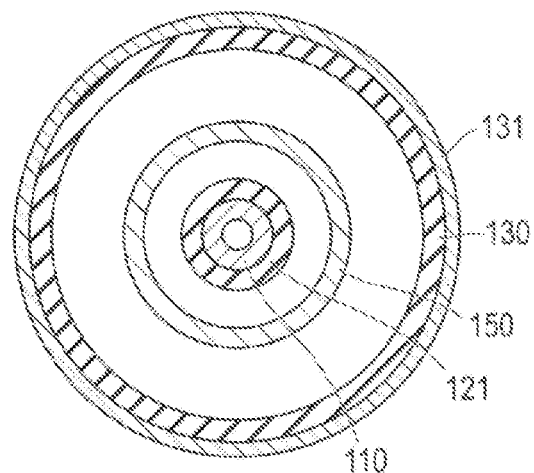
FIG. 9 is a cross-sectional view taken along line 9-9 of FIG. 6.

As shown in FIGS. 7 to 9, the intermediate member 120 is disposed in the outer circumferential portion of the urethral catheter 110 so as to be able to slide on and be fixed to the urethral catheter 110.

Figure 10:
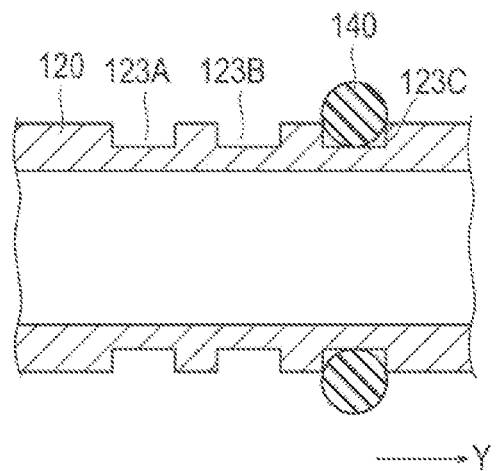
FIG. 10 is a front sectional view of the portion A of FIG. 6.

As shown in FIG. 10, the intermediate member 120 can have three grooves (holding portions) 123A, 123B, and 123C with which the restriction portion 140 can interlock. Herein, FIG. 10 shows a state in which the restriction portion 140 has interlocked with the groove 123C.

The tubular member 150 can be fixed to the proximal side of the intermediate member 120 in the Y-direction. The tubular member 150 can be fixed to the intermediate member 120 by means of, for example, bonding using an adhesive or heat-welding.

As the material constituting the intermediate member 120, the same material as the material constituting the urethral catheter 110 can be used.

As shown in FIG. 8, an intermediate balloon 121, which presses the urethral catheter 110 by dilating inward such that the tubular member 150 is fixed to the urethral catheter 110, is provided in the inner circumferential portion of the tubular member 150. Furthermore, the tubular member 150 is provided with a hole portion 151. The hole portion 151 may be a plurality of holes or the like that is in the form of mesh.

On the proximal side in the Y-direction, the intermediate balloon 121 is fixed to the tubular member 150 by an adhesive, and on the distal side in the Y-direction, the intermediate balloon 121 is fixed to the tubular member 150 and the intermediate member 120 by an adhesive. In FIG. 8, the two-dot chain line shows the intermediate balloon 121 having not yet been deformed by dilation, and the solid line shows the intermediate balloon 121 having been deformed by dilation.

As the material constituting the intermediate balloon 121, the same material as the material constituting the distal side balloon 111 can be used.

As shown in FIG. 8, on the proximal side in the Y-direction, the balloon 130 is fixed to the tubular member 150 by an adhesive, and on the distal side in the Y-direction, the balloon 130 is fixed to the tubular member 150 and the intermediate member 120 by an adhesive. The medical material 131 providing the epithelial function is held in the outer circumferential portion of the balloon 130.

In the inner circumferential portion of the balloon 130, a tube 132 is disposed which can include a lumen 132L for feeding a dilation medium into an internal space 130A of the balloon 130. In FIG. 8, the two-dot chain line shows the balloon 130 having not yet been deformed by dilation, and the solid line shows the balloon 130 having been deformed by dilation. Through the lumen 132L, a dilation medium is fed into the internal space 130A of the balloon 130, and as a result, the balloon 130 dilates outward. In this way, the medical material 131 can indwell in the urethra 10, in a state of coming into contact with the inner wall 11 of the urethra 10. Furthermore, through the hole 151, a dilation medium is fed into an internal space 121A of the intermediate balloon 121. In this way, the intermediate balloon 121 dilates inward, and the tubular member 150 and the intermediate member 120 are fixed to the urethral catheter 110. In accordance with an exemplary embodiment, for example, the balloon 130 and the restriction portion 140 are fixed to the urethral catheter 110.

As the material constituting the balloon 130, the same material as the material constituting the distal side balloon 111 or the intermediate balloon 121 can be used.

As the material constituting the tube 132, the same material as the material constituting the urethral catheter 110 or a tube 122 can be used.

As shown in FIG. 10, the restriction portion 140 is an O ring (cyclic member). The restriction portion 140 interlocks with any of the three grooves 123A, 123B, and 123C provided in the intermediate member 120, and comes into contact with the external urethral sphincter 18 in the living body. In this way, the restriction portion 140 restricts the movement of the medical material 131 toward the distal side in the Y-direction. The restriction portion 140 can move on the intermediate member 120 so as to be able to interlock with any of the three grooves 123A, 123B, and 123C. Therefore, the restriction portion 140 is constituted such that it can move relative to the balloon 130 in the Y-direction. Accordingly, if the restriction portion 140 can be appropriately moved according to the individual difference of the patient, the medical material 131 can selectively indwell at different treatment sites 30A, and the procedure becomes relatively easier. Herein, the restriction portion 140 may not be able to move on the intermediate member 120.

In accordance with an exemplary embodiment, the outer diameter of the restriction portion 140 is approximately identical to the inner diameter of the bulbous urethra 15 of the step S formed due to a difference of inner diameter that occurs in the boundary between the bulbous urethra 15 and the membranous portion 16 of the urethra (see FIGS. 11A and 11B). Furthermore, the inner diameter of the restriction portion 140 can be approximately identical to the outer diameter of the grooves 123A, 123B, and 123C (see FIG. 10).

Next, how to use the urethral stricture treatment apparatus 1 according to the first embodiment will be described with reference to FIGS. 11A and 11B. In FIGS. 11A and 11B, in order to facilitate easy understanding, the urethral stricture treatment apparatus 1 is shown in a front view, and the urethra 10 is shown in a front sectional view.

Before inserting the urethral stricture treatment apparatus 1 according to the first embodiment into the urethra 10, an operator observes the inside of the urethra 10 by inserting an endoscope known in the medical field into the urethra 10. In this state, through a channel provided in the endoscope, the operator inserts a predetermined treatment tool into the urethra 10. Thereafter, by using the predetermined treatment tool inserted into the urethra 10, the operator provides a treatment such as incision, cutting, excision or the like to the scar tissue 31 formed in the urethra 10. In this way, the operator treats the stenosed site 30 and forms the treatment site 30A. The operator then measures a distance L1 between the position, in which the step S formed due to a difference of inner diameter occurs in the boundary between the bulbous urethra 15 and the membranous portion 16 of the urethra, and the treatment site 30A.

Thereafter, based on the distance L1 between the position in which the step S formed due to a difference of inner diameter occurs and the treatment site 30A, the operator causes the restriction portion 140 to interlock with any of the three grooves 123A, 123B, and 123C provided in the intermediate member 120. FIGS. 11A and B show a state in which the restriction portion 140 has interlocked with the groove 123C.

Subsequently, the operator winds the rectangular medical material 131 providing the epithelial function around the outer circumferential portion of the balloon 130, thereby mounting the medical material 131 on the outer circumferential portion of the balloon 130.

The operator then inserts the urethral stricture treatment apparatus 1 into the urethra 10 in a state in which the intermediate balloon 121 and the distal side balloon 111 have contracted as shown in FIG. 11A, and brings the restriction portion 140 into contact with the step S formed due to a difference of inner diameter. At this time, the restriction portion 140 has interlocked with the groove 123C based on the distance L1. Therefore, in the state in which the restriction portion 140 comes into contact with the step S formed due to a difference of inner diameter, the medical material 131 is positioned and disposed in the treatment site 30A. At this time, by inserting an endoscope into the lumen 112, the operator can insert the urethral stricture treatment apparatus 1 into the urethra 10 while observing the form of the urethra 10.

Thereafter, as shown in FIG. 11B, the operator dilates the distal side balloon 111, pushes the intermediate member 120, the balloon 130, the restriction portion 140, and the tubular member 150 into the distal side in the Y-direction, dilates the intermediate balloon 121 while pulling the urethral catheter 110 to the proximal side in the Y-direction, and fixes the balloon 130 and the restriction portion 140 to the urethral catheter 110. As a result, the distal side balloon 111 comes into contact with the internal urethral sphincter 19, the restriction portion 140 comes into contact with the external urethral sphincter 18, and in this state, the medical material 131 providing the epithelial function indwells at the treatment site 30A while coming into contact with the treatment site 30A. Consequently, the position of the medical material 131 can be prevented from deviating from the treatment site 30A. In this way, by making the medical material 131 providing the epithelial function indwell at the treatment site 30A in a state of coming into contact with the treatment site 30A, epithelial cells can be engrafted into the treatment site 30A and the restenosis of the treatment site 30A can be prevented.

Subsequently, the operator contracts the distal side balloon 111 and the balloon 130, and then pulls the urethral stricture treatment apparatus 1 out of the urethra 10.

As described above, the urethral stricture treatment apparatus 1 according to the present exemplary embodiment is a treatment apparatus for treating the urethral stricture. The urethral stricture treatment apparatus 1 has the balloon 130, which dilates in a state of holding the medical material 131 providing the epithelial function so as to bring the medical material 131 into contact with the inner wall 11 of the urethra 10, and the restriction portion 140 which is provided in a position closer to the distal side than the balloon 130 in the Y-direction such that the distance between the restriction portion 140 and the balloon 130 can be relatively changed, and comes into contact with the external urethral sphincter 18 in the living body so as to restrict the movement of the medical material 131 toward the distal side. According to this constitution, when the medical material 131 indwells at the treatment site 30A, the restriction portion 140 comes into contact with the external urethral sphincter 18 in the living body so as to restrict the movement of the medical material 131 toward the distal side. Therefore, the suturing procedure which is a treatment method exemplified in the section of Background Art is not required, and the position of the medical material 131 can be relatively easily inhibited from deviating from the treatment site 30A toward the distal side in the Y-direction. Furthermore, the restriction portion 140 is provided such that the distance between the restriction portion 140 and the balloon 130 can be relatively changed. Consequently, the distance between the restriction portion 140 and the balloon 130 can be appropriately set according to the individual difference of the patient, and the medical material 131 can be selectively indwelled at different treatment sites 30A. Accordingly, the urethral stricture treatment apparatus 1 can be provided which can relatively easily inhibit the position of the medical material 131 from deviating from the treatment site 30A toward the distal side in the Y-direction, and can make the medical material 131 selectively indwell at different treatment sites 30A.

The urethral stricture treatment apparatus 1 further has the flexible and long urethral catheter 110, which enables the balloon 130 and the restriction portion 140 to be fixed thereto and can be inserted into the urethra 10, and the distal side balloon 111 which is provided in a position closer to the distal side than the restriction portion 140 in the Y-direction within the urethral catheter 110 and comes into contact with the internal urethral sphincter 19 in the living body so as to restrict the movement of the medical material 131 toward the proximal side in the Y-direction. According to this constitution, within the urethral catheter 110, which enables the balloon 130 and the restriction portion 140 to be fixed to the urethral catheter 110, the distal side balloon 111 is provided in a position closer to the distal side than the restriction portion 140. Therefore, when the medical material 131 indwells at the treatment site 30A, the distal side balloon 111 comes into contact with the internal urethral sphincter 19 in the living body, and in this way, the movement of the medical material 131 toward the proximal side is restricted. As a result, the position of the medical material 131 can be relatively easily inhibited from deviating from the treatment site 30A toward the proximal side in the Y-direction.

The urethral catheter 110 is constituted with a transparent or semitransparent member, and the lumen 112 into which an endoscope can be inserted is provided inside the urethral catheter 110. Therefore, the operator can perform a procedure while observing the form of the urethra 10 by using the endoscope, and accordingly, the procedure becomes relatively easier.

The balloon 130 further has the intermediate member 120 including the grooves 123A, 123B, and 123C that can hold the restriction portion 140, and the restriction portion 140 is an O ring fixed by being held in the grooves 123A, 123B, and 123C. Therefore, by a simple structure, the movement of the medical material toward the distal side in the insertion direction can be restricted.

The restriction portion 140 is constituted such that it can move relative to the balloon 130 in the Y-direction. Accordingly, by appropriately moving the restriction portion 140 relative to the balloon 130 according to the individual difference of the patient, the medical material 131 can be made selectively indwell at different treatment sites 30A, and the procedure becomes relatively easier.

As described above, the urethral stricture treatment method according to the present embodiment is a urethral stricture treatment method for treating the urethral stricture. The urethral stricture treatment method can include an insertion step of inserting the urethral stricture treatment apparatus 1, which includes the balloon 130 that can dilate in a state of holding the medical material 131 providing the epithelial function and the restriction portion 140 that is disposed in a position closer to the distal side than the balloon 130 and restricts the movement of the medical material 131 toward the distal side in the Y-direction, into the urethra 10, a contact step of bringing the restriction portion 140 into contact with the external urethral sphincter 18 in the living body; an adjustment step of adjusting the distance between the balloon 130 and the restriction portion 140, and a contact step of bringing the medical material 131 into contact with the treatment site 30A by dilating the balloon 130. According to the urethral stricture treatment method, the position of the medical material 131 can be relatively easily inhibited from deviating from the treatment site 30A and the medical material 131 can be selectively indwelled at different treatment sites 30A.

In the adjustment step, the distance between the balloon 130 and the restriction portion 140 is adjusted by moving the restriction portion 140 relative to the balloon 130. Therefore, by appropriately moving the restriction portion 140 according to the individual difference of the patient, the medical material 131 can be selectively indwelled at different treatment sites 30A.

Next, a urethral stricture treatment apparatus 2 according to a second exemplary embodiment of the present disclosure will be described. Hereinafter, the portions common to the first and second embodiments will not be described, and only the portions unique to the second embodiment will be described. The urethral stricture treatment apparatus 2 according to the second embodiment is different from the urethral stricture treatment apparatus 1 according to the first embodiment in that a balloon 230 is constituted so as to be able to move relative to a restriction portion 240. Furthermore, the urethral stricture treatment apparatus 2 is different from the urethral stricture treatment apparatus 1 in terms of the constitution of an intermediate member 220 and the constitution of the restriction portion 240.

Figure 12:
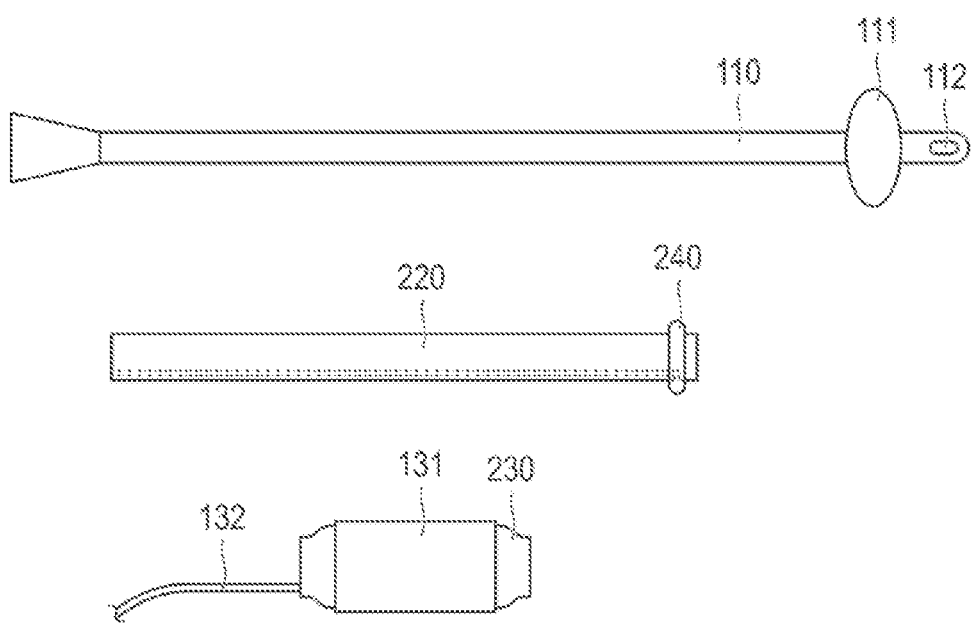
FIG. 12 is an exploded view showing a urethral stricture treatment apparatus according to a second exemplary embodiment of the present disclosure.
Figure 13:
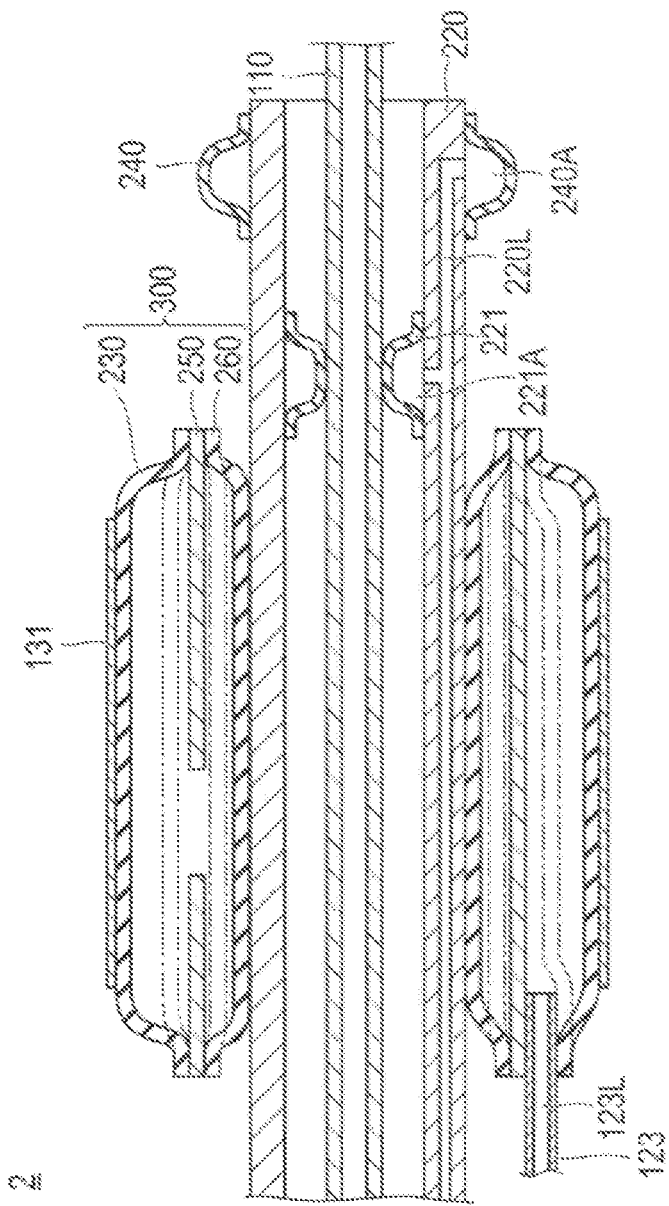
FIG. 13 is a front sectional view showing the urethral stricture treatment apparatus according to the second exemplary embodiment.

FIG. 12 is an exploded view showing the urethral stricture treatment apparatus 2 according to the second embodiment. FIG. 13 is a front sectional view showing the urethral stricture treatment apparatus 2 according to the second embodiment.

As shown in FIGS. 12 and 13, the urethral stricture treatment apparatus 2 according to the second embodiment has the urethral catheter 110, the intermediate member (fixing member) 220, the balloon 230, the restriction portion 240, a tubular member 250, and a second intermediate balloon 260. The urethral catheter 110 has the same constitution as the urethral catheter 110 according to the first embodiment, and therefore the description thereof will not be repeated.

As shown in FIG. 13, the intermediate member 220 is disposed such that it can slide on and be fixed to the urethral catheter 110. In the inner circumferential portion of the intermediate member 220, a first balloon (fixing balloon) 221 is provided which presses and holds the urethral catheter 110 by dilating inward. Furthermore, the intermediate member 220 has a lumen 220L, which is for dilating the first intermediate balloon 221 and the restriction portion 240, in the tube wall of the intermediate member 220. For example, when a dilation medium is fed into an internal space 221A of the first intermediate balloon 221 through the lumen 220L, the first intermediate balloon 221 dilates, and the intermediate member 220 is fixed to the urethral catheter 110.

The balloon 230 and the second intermediate balloon 260 constitute a balloon device 300 by being fixed to the tubular member 250 by an adhesive or heat-welding. The balloon device 300 is constituted such that it can slide on and be fixed to the outer circumferential portion of the intermediate member 220. By dilating inward, the second intermediate balloon 260 presses the intermediate member 220, and as a result, the balloon device 300 is fixed to the intermediate member 220. The constitution of the balloon 230, the tubular member 250, and the second intermediate balloon 260 is the same as the constitution of the balloon 130, the tubular member 150, and the intermediate balloon 121 according to the first embodiment, and therefore the description thereof will not be repeated.

The restriction portion 240 is a balloon constituted so as to be able to be deformed by dilation. On the distal side in the Y-direction, the restriction portion 240 is fixed to the outer circumferential portion of the intermediate member 220 by an adhesive or heat-welding. When a dilation medium is fed into an internal space 240A of the restriction portion 240 through the lumen 220L provided in the intermediate member 220, the restriction portion 240 dilates and comes into contact with the external urethral sphincter 18 in the living body, and in this way, the restriction portion 240 restricts the movement of the medical material 131 toward the distal side in the Y-direction (see FIG. 15).

Figure 15:
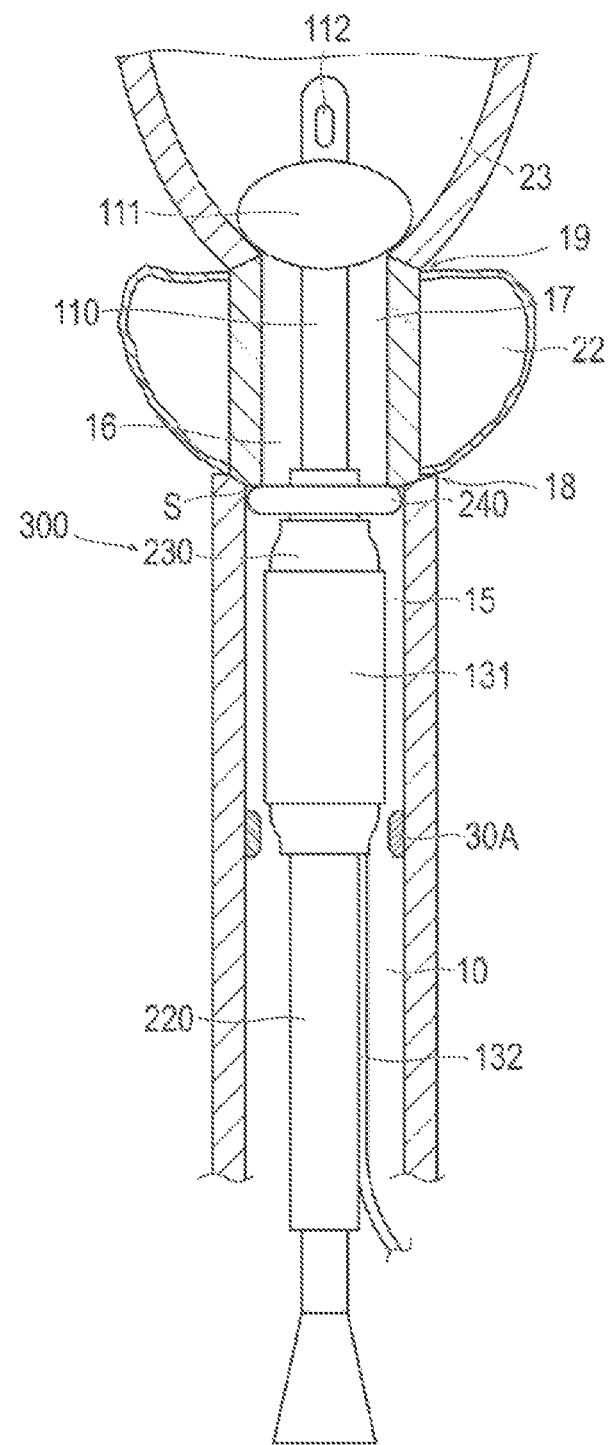
FIG. 15 is a view showing a state in which the distal side balloon and the restriction portion come into contact with the internal urethral sphincter and the external urethral sphincter respectively.

The outer diameter of the dilated restriction portion 240 is approximately identical to the inner diameter of the bulbous urethra 15 of the step S formed due to a difference of diameter that occurs in the boundary between the bulbous urethra 15 and the membranous portion 16 of the urethra (see FIG. 15).

In the aforementioned constitution, the balloon 230 is constituted such that it can move relative to the restriction portion 240 in the Y-direction (insertion direction). Accordingly, by appropriately moving the balloon 230 in the Y-direction according to the individual difference of the patient, the medical material 131 can be selectively indwelled different treatment sites 30A, and the procedure becomes relatively easier.

Next, how to use the urethral stricture treatment apparatus 2 according to the second embodiment will be described with reference to FIGS. 14 to 17. Because the steps performed by the time the treatment site 30A is formed and the step of mounting the medical material 131 on the balloon 230 are conducted in the same manner as in the first embodiment 1, the description thereof will not be repeated.

Figure 14:
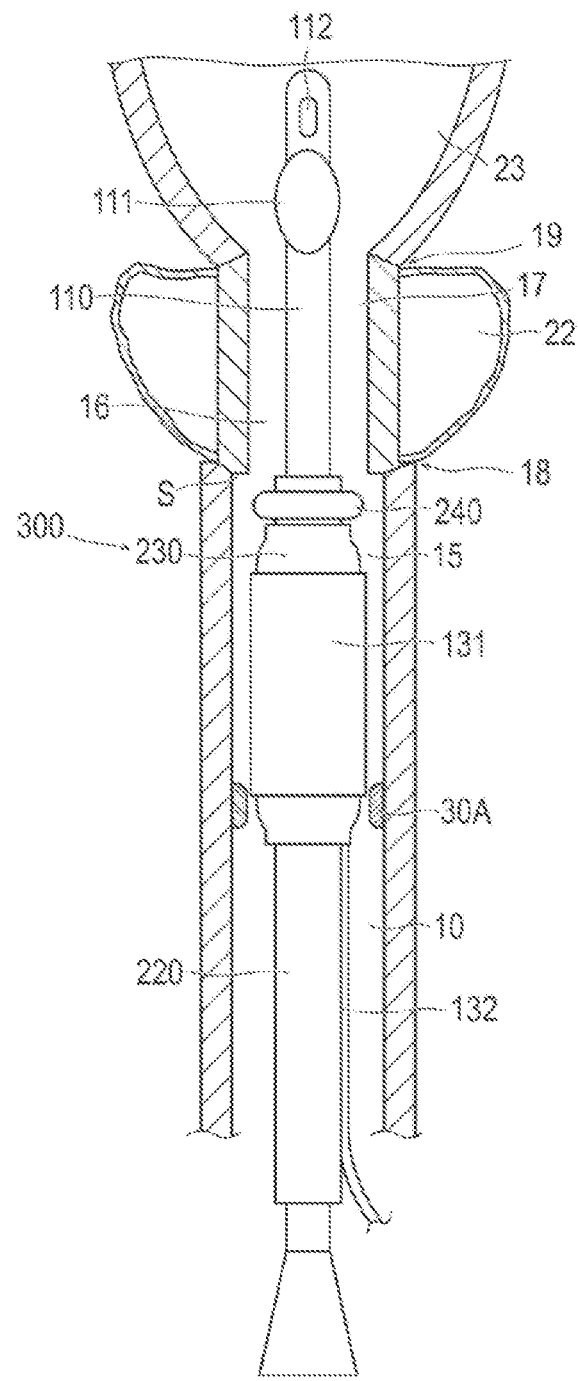
FIG. 14 is a view showing the way the urethral stricture treatment apparatus is inserted into the urethra in a state in which a distal side balloon and a restriction portion have contracted.

As shown in FIG. 14, in a state in which the distal side balloon 111, the balloon 230, the restriction portion 240, the first intermediate balloon 221, and the second intermediate balloon 260 have contracted, the operator inserts the urethral stricture treatment apparatus 2 into the urethra 10. At this time, the distal side balloon 111 is disposed in a position closer to the distal side than the internal urethral sphincter 19 in the Y-direction. Unlike the urethral stricture treatment apparatus 1 according to the first embodiment, the urethral stricture treatment apparatus 2 according to the second embodiment can be inserted into the urethra 10 in a state in which the restriction portion 240 has contracted. Therefore, the urethral stricture treatment apparatus 2 can be inserted into the urethra 10 in a relatively less invasive manner, and the strain imposed on the patient can be relatively reduced.

Thereafter, as shown in FIG. 15, the operator dilates the distal side balloon 111, and in a state in which the position of the intermediate member 220, the balloon device 300, the medical material 131, and the restriction portion 240 is fixed, the operator pulls out the urethral catheter 110 toward the proximal side in the Y-direction and brings the distal side balloon 111 into contact with the internal urethral sphincter 19. Thereafter, in a state in which the position of the urethral catheter 110 is fixed, the operator pushes the intermediate member 220, the balloon device 300, the medical material 131, and the restriction portion 240 toward the distal side. At the same time, the operator feeds a dilation medium into the restriction portion 240 through the lumen 220L, thereby dilating the restriction portion 240 and bringing the restriction portion 240 into contact with the step S formed due to a difference of inner diameter. When the dilation medium is fed into the restriction portion 240 through the lumen 220L, the restriction portion 240 and the first intermediate balloon 221 dilate. As a result, the intermediate member 220 is fixed to the urethral catheter 110. Herein, during the procedure, it is preferable to dilate the restriction portion 240 while pushing the restriction portion 240 toward the distal side in the Y-direction and pulling the urethral catheter 110 toward the proximal side in the Y-direction.

Figure 16:
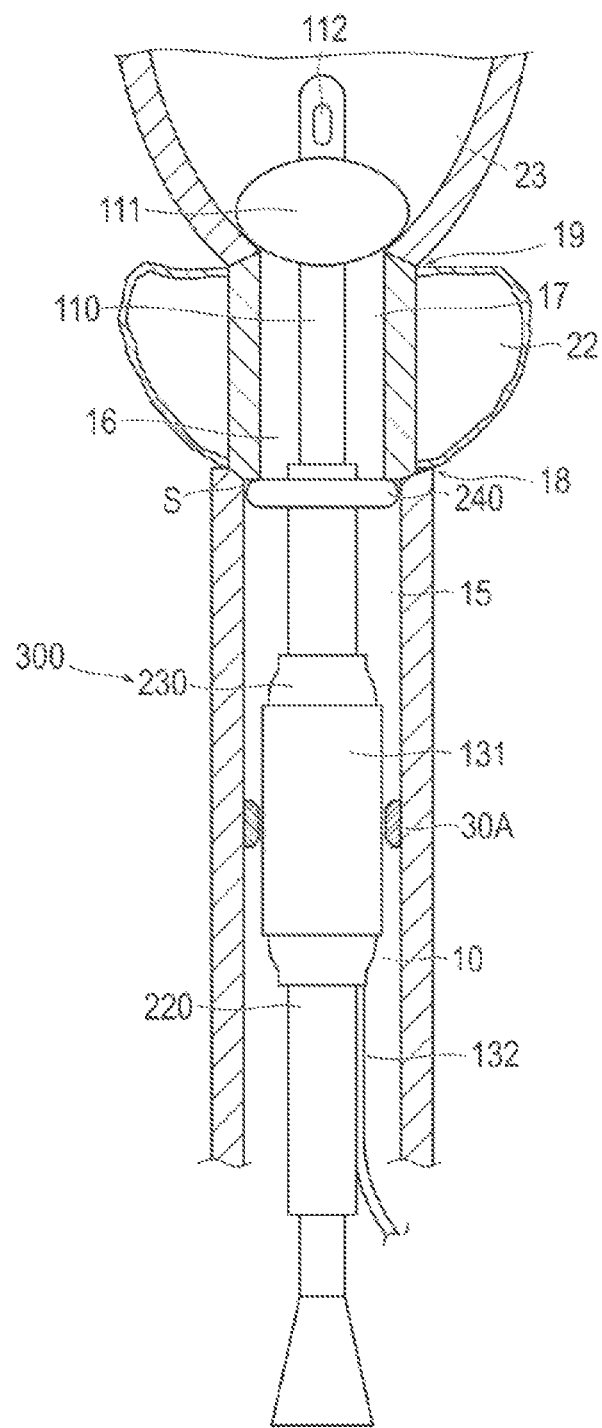
FIG. 16 is a view showing a state in which a balloon is disposed in the inner circumferential portion of the treatment site.

Subsequently, as shown in FIG. 16, in a state in which the position of the urethral catheter 110, the intermediate member 220, and the restriction portion 240 is fixed, the operator pulls out the balloon device 300 toward the proximal side in the Y-direction, and positions and disposes the medical material 131 in the treatment site 30A. At this time, by inserting an endoscope in the lumen 112, the operator can pull out the balloon device 300 toward the proximal side in the Y-direction while observing the state of the urethra 10.

Figure 17:
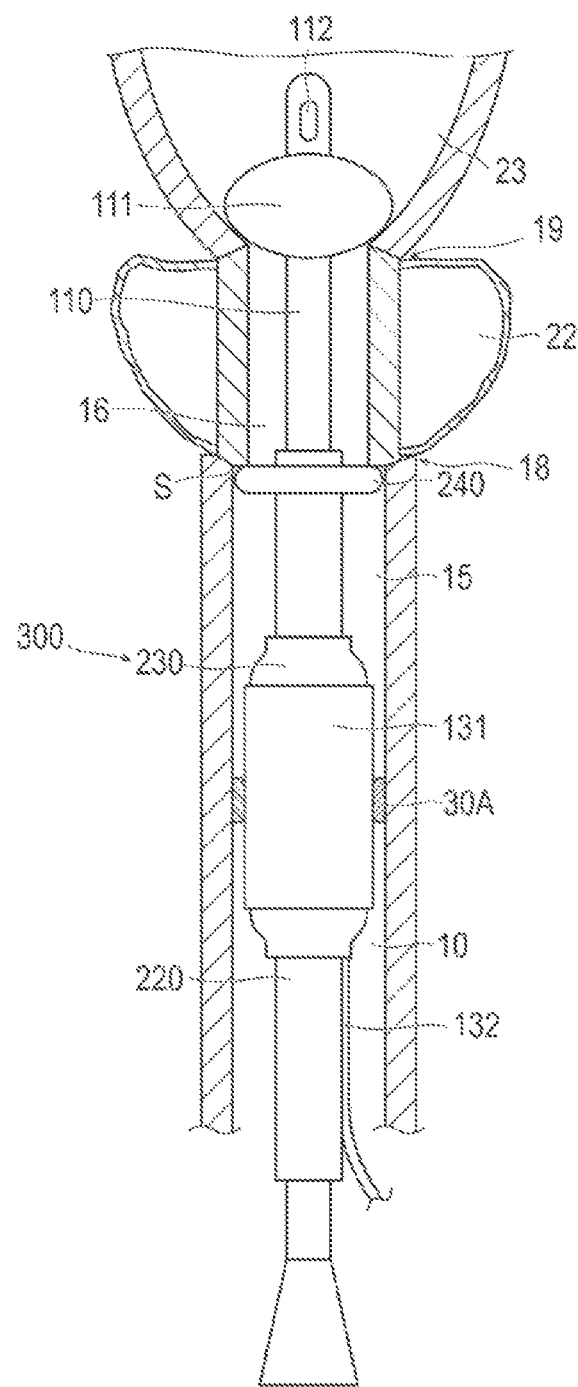
FIG. 17 is a view showing a state in which the balloon has dilated.

Then, as shown in FIG. 17, by feeding a dilation medium into the apparatus through the lumen 132L, the operator dilates the balloon 230 and the second intermediate balloon 260. When the balloon 230 dilates, the medical material 131 indwells the treatment site 30A for a predetermined period of time in a state of coming into contact with the treatment site 30A. Furthermore, when the second intermediate balloon 260 dilates, the balloon device 300 is fixed to the intermediate member 220. As a result of the procedure, in a state in which the distal side balloon 111 and the restriction portion 240 come into contact with the internal urethral sphincter 19 and the external urethral sphincter 18 respectively, the medical material 131 indwells the treatment site 30A. Consequently, the position of the medical material 131 can be prevented from deviating from the treatment site 30A.

Thereafter, the operator contracts the distal side balloon 111, the balloon 230, and the restriction portion 240, and then pulls the urethral stricture treatment apparatus 2 out of the urethra 10.

As described above, the urethral stricture treatment apparatus 2 according to the second embodiment further has the intermediate member 220 provided with the restriction portion 240 in the outer circumferential portion of the intermediate member 220, and the first intermediate balloon 221 which is disposed in the inner circumferential portion of the intermediate member 220 and dilates in the circumferential direction of the intermediate member 220 so as to fix the intermediate member 220 and the urethral catheter 110. Therefore, by the first intermediate balloon 221, the intermediate member 220 and the urethral catheter 110 can be reliably fixed.

The balloon 230 is constituted such that it can move relative to the restriction portion 240 in the Y-direction. Consequently, by appropriately moving the balloon 230 relative to the restriction portion 240 according to the individual difference of the patient, the medical material 131 can be selectively indwelled different treatment sites 30A, and the procedure becomes relatively easier.

The restriction portion 240 is constituted such that it can be deformed by dilation. Therefore, unlike the urethral stricture treatment apparatus 1 according to the first embodiment, the urethral stricture treatment apparatus 2 according to the second embodiment can be inserted into the urethra 10 in a state in which the restriction portion 240 has contracted. Consequently, the urethral stricture treatment apparatus 2 can be inserted into the urethra 10 in a relatively less invasive manner, and the strain imposed on the patient can be reduced.

The restriction portion 240 is a balloon. Therefore, the medical material 131 can be inhibited from moving toward the distal side in the Y-direction by a simple structure.

As described above, in the adjustment step of the urethral stricture treatment method according to the present embodiment, in a state in which the restriction portion 240 comes into contact with the external urethral sphincter 18, the balloon 230 is moved relative to the restriction portion 240, thereby adjusting the distance between the balloon 230 and the restriction portion 240. Therefore, by appropriately moving the balloon 230 according to the individual difference of the patient, the medical material 131 can be selectively indwelled at different treatment sites 30A.

The present invention is not limited to the aforementioned embodiments, and can be modified in various ways within the scope of claims.

In the aforementioned embodiments, an O ring was used as the restriction portion 140 of the first embodiment, and a balloon was used as the restriction portion 240 of the second embodiment. However, a balloon may be used as the restriction portion of the first embodiment, and an O ring may be used as the restriction portion of the second embodiment.

In the first embodiment, the intermediate member 120 had three grooves 123A, 123B, and 123C with which the restriction portion 140 can interlock. However, the restriction portion 140 may have two grooves or four or more grooves.

In the first embodiment, the urethral catheter 110, the intermediate member 120, the balloon 130, the restriction portion 140, and the tubular member 150 were simultaneously inserted into the urethra. However, the intermediate member 120, the balloon 130, the restriction portion 140, and the tubular member 150 may be inserted into the urethra first, the balloon 130 is then positioned in the treatment site 30A, and thereafter the urethral catheter 110 may be inserted into the urethra. Likewise, in the second embodiment, the urethral catheter 110 may be inserted later into the urethra.

In the first and second embodiments, the tubular member 150 was provided. However, a constitution may be adopted in which the tubular member 150 is not provided in the balloon 130.

In the second embodiment, by dilating the second intermediate balloon 260 and the first intermediate balloon 221 inward, the balloon 230, the intermediate member 220, and the urethral catheter 110 were integrally fixed. However, an embodiment may be adopted in which the intermediate member 220 is constituted with a material with low rigidity, and the second intermediate balloon 260 dilates inward so as to press the intermediate member 220 and the urethral catheter 110, thereby integrally fixing the balloon 230, the intermediate member 220, and the urethral catheter 110. At this time, a constitution may be adopted in which the intermediate member 220 is provided with a slit or a window that is disposed in a portion of the intermediate member 220, such that the pressing force of the second intermediate balloon 260 is effectively transmitted to the urethral catheter 110.

The restriction portion is not particularly limited, as long as it is constituted such that the size of the restriction portion is larger than that of the intermediate members 120 and 220 in the radial direction, and the restriction portion comes into contact with the external urethral sphincter 18 so as to restrict the movement of the medical material 131 toward the distal side in the Y-direction.

The material constituting the urethral stricture treatment apparatuses 1 and 2 may be mixed with a radiopaque material such as barium sulfate, bismuth sulfate, or tungsten. If such a material is used, the insertion state of the urethral stricture treatment apparatuses 1 and 2, the position of the urethral stricture treatment apparatuses 1 and 2, and the like can be relatively easily confirmed under the X rays.

Hereinafter, exemplary modifications of the aforementioned embodiments will be described.

Figure 18:
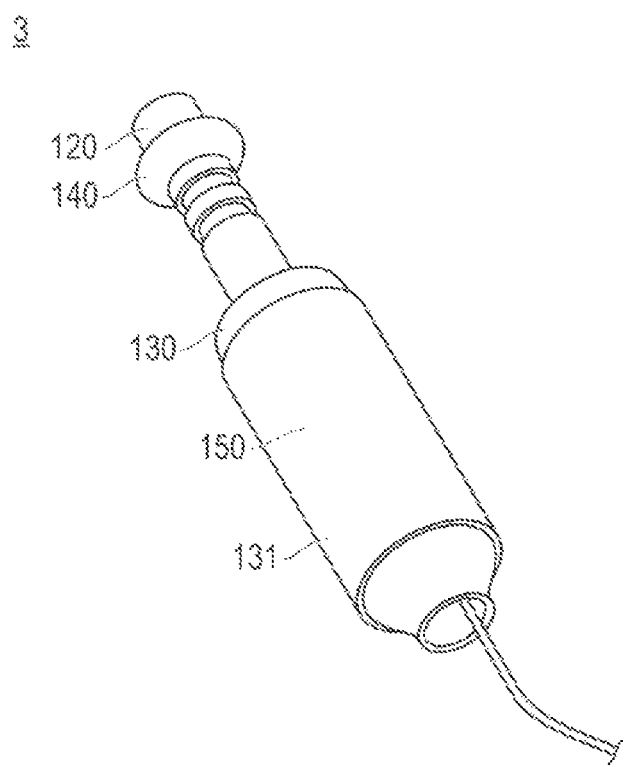
FIG. 18 is a perspective view showing a urethral stricture treatment apparatus according to a first exemplary modification.
Figure 19:
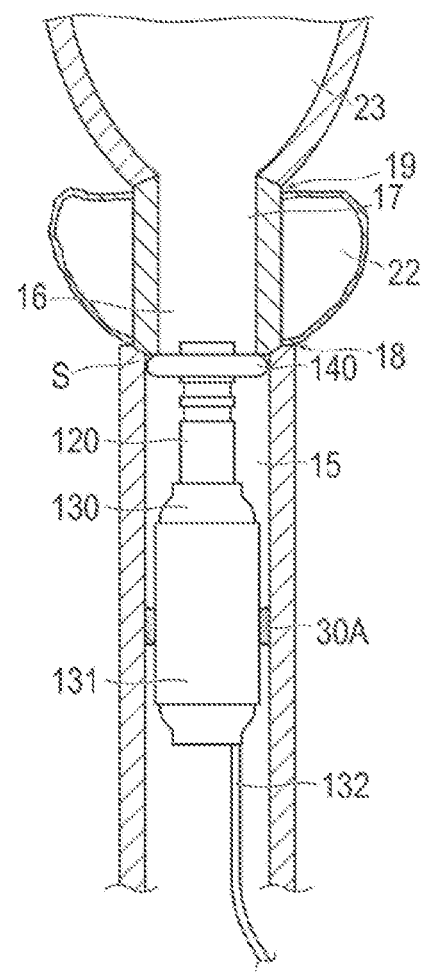
FIG. 19 is a view for illustrating a procedure using the urethral stricture treatment apparatus according to the first exemplary modification.

FIG. 18 is a perspective view showing a urethral stricture treatment apparatus 3 according to a first exemplary modification. In the first embodiment, the urethral stricture treatment apparatus 1 had the urethral catheter 110, the intermediate member 120, the balloon 130, the restriction portion 140, and the tubular member 150. However, as shown in FIG. 18, the urethral stricture treatment apparatus may be constituted with the intermediate member 120, the balloon 130, the restriction portion 140, and the tubular member 150. According to this constitution, when the medical material 131 indwells the treatment site 30A, the restriction portion 140 comes into contact with the external urethral sphincter 18 in the living body as shown in FIG. 19, and in this way, the movement of the medical material 131 toward the distal side can be restricted by a simpler structure.

Figure 20:
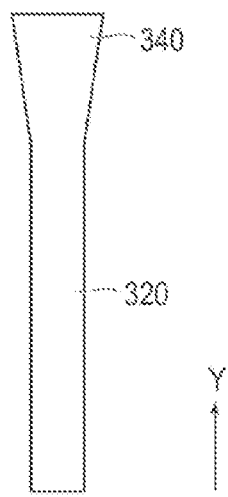
FIG. 20 is a view showing a restriction portion according to a second exemplary modification.

FIG. 20 is a schematic view showing a restriction portion 340 provided on the distal side of an intermediate member 320 according to a second exemplary modification. In the second embodiment, the restriction portion 240 was a balloon constituted so as to be able to be deformed by dilation. However, as shown in FIG. 20, the restriction portion 340 may be constituted such that it is provided at the distal end in the Y-direction and has a tapered shape in which the diameter of the restriction portion 340 increases toward the distal side in the Y-direction. According to this constitution, unlike the case of using the urethral stricture treatment apparatus 2 according to the second embodiment, the procedure of dilating the restriction portion 340 can be skipped. Therefore, the procedure becomes relatively easier.

Figure 21A:
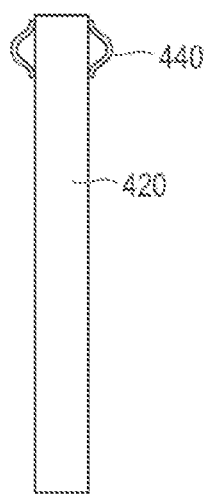
FIG. 21A is a view showing a restriction portion according to a third exemplary modification.
Figure 21B:
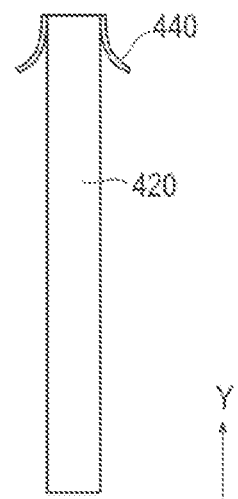
FIG. 21B is a view showing a restriction portion according to the third exemplary modification.

FIGS. 21A and 21B are schematic views showing a restriction portion 440 provided on the distal side of an intermediate member 420 according to a third exemplary modification. As shown in FIGS. 21A and 21B, the restriction portion 440 according to the third exemplary modification may be en elastic material that is provided at the distal end in the Y-direction and can be deformed by dilating outward in the radial direction. When the urethral stricture treatment apparatus is inserted into the urethra, the outer circumferential portion of the restriction portion 440 as an elastic material is covered with a tube sheath not shown in the drawing, and thus the restriction portion is disposed inside the tube sheath in a contracted state. After the restriction portion 440 reaches the vicinity of the step S formed due to a difference of inner diameter on the proximal side, the tube sheath is removed. As a result, the restriction portion 440 dilates outward in the radial direction and comes into contact with the external urethral sphincter 18. According to this constitution, unlike the case of using the urethral stricture treatment apparatus 1 according to the first embodiment, the urethral stricture treatment apparatus of this example can be inserted into the urethra in a state in which the restriction portion 440 has contracted. Consequently, the urethral stricture apparatus can be inserted into the urethra in a relatively less invasive manner, and the strain imposed on the patient can be reduced.

Figure 22:
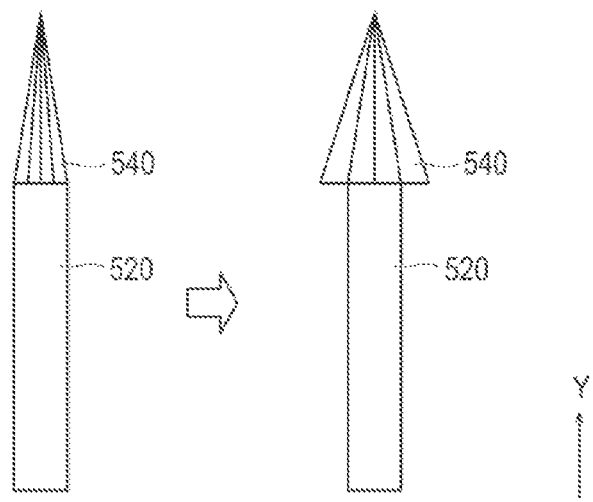
FIG. 22 is a view showing a restriction portion according to a fourth exemplary modification.

FIG. 22 is a schematic view showing a restriction portion 540 provided on the distal side of an intermediate member 520 according to a fourth exemplary modification. As shown in FIG. 22, the restriction portion 540 according to the fourth exemplary modification may be in the form of an umbrella that is provided at the distal end in the Y-direction and can be deformed by dilating outward in the radial direction. When the urethral stricture treatment apparatus is inserted into the urethra, the outer circumferential portion of the restriction portion 540 in the form of an umbrella is covered with a tube sheath not shown in the drawing, and thus the restriction portion is disposed inside the tube sheath in a contracted state. A constitution may be adopted in which the shape of the umbrella shown in FIG. 22 is upside down. After the restriction portion 540 reaches the vicinity of the step S formed due to a difference of inner diameter on the proximal side, the tube is removed. As a result, the restriction portion 540 dilates outward in the radial direction and comes into contact with the external urethral sphincter 18. According to this constitution, unlike the urethral stricture treatment apparatus 1 according to the first embodiment, the urethral stricture treatment apparatus of this example can be inserted into the urethra in a state in which the restriction portion 540 has contracted. Consequently, the urethral stricture treatment apparatus can be inserted into the urethra in a less invasive manner, and the strain imposed on the patient can be reduced.

Figure 23:
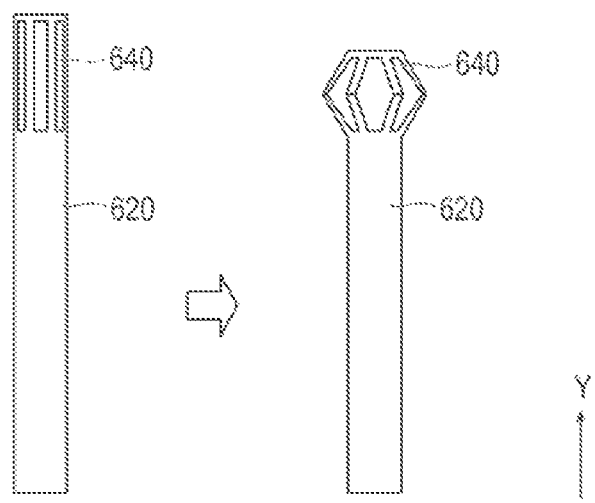
FIG. 23 is a view showing a restriction portion according to fifth exemplary modification.

FIG. 23 is a schematic view showing a restriction portion 640 according to a fifth exemplary modification. As shown in FIG. 23, the restriction portion 640 according to the fifth exemplary modification may be constituted such that it is formed on the distal side of an intermediate member 620, in which a plurality of groove shapes extending in the Y-direction is formed in the circumferential direction on the distal side of the Y-direction, so as to correspond to the groove shapes. In this constitution, a rod-like member (not shown in the drawing), which can be bonded to the distal side of the intermediate member 620, is inserted into the intermediate member 620, the distal end of the rod-like member is bonded to the distal end of the intermediate member 620, and in this state, the rod-like member is pulled out toward the proximal side. As a result, the restriction portion 640 is deformed by dilating outward in the radial direction and comes into contact with the external urethral sphincter 18. According to this constitution, unlike the urethral stricture treatment apparatus 1 according to the first embodiment, the urethral stricture treatment apparatus of this example can be inserted into the urethra in a state in which the restriction portion 640 has not contracted. Consequently, the urethral stricture treatment apparatus can be inserted into the urethra in a less invasive manner, and the strain imposed on the patient can be reduced.

The detailed description above describes a urethral stricture treatment apparatus and a urethral stricture treatment method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A urethral stricture treatment apparatus for treating urethral stricture, the urethral stricture treatment apparatus comprising:
    a dilation portion which dilates in a state of holding a medical material providing an epithelial function so as to bring the medical material into contact with an inner wall of the urethra; and
    a restriction portion which is in a position closer to a distal side than the dilation portion in an insertion direction such that a distance between the restriction portion and the dilation portion can be relatively changed, and comes into contact with external urethral sphincter in a living body so as to restrict the movement of the medical material toward the distal side;
    a flexible main body portion which enables the dilation portion and the restriction portion to be fixed to the main body portion and insertable into the urethra;
    a distal side restriction portion which is in a position closer to the distal side than the restriction portion within the main body portion and comes into contact with internal urethral sphincter in the living body so as to restrict the movement of the medical material toward a proximal side in the insertion direction;
    fixing member with the restriction portion in the outer circumferential portion of the fixing member; and
    a fixing balloon which is arranged in the inner circumferential portion of the fixing member and dilates in a circumferential direction so as to fix the fixing member and the main body portion.

2. The urethral stricture treatment apparatus according to claim 1, wherein
    the main body portion is a transparent or a semitransparent member, and
    an insertion lumen into which an endoscope can be inserted inside the main body portion.

3. The urethral stricture treatment apparatus according to claim 1, wherein
    the dilation portion has a holding member including a holding portion that is configured to hold the restriction portion, and
    the restriction portion is a cyclic member which is fixed by being held in the holding portion.

4. The urethral stricture treatment apparatus according to claim 1, wherein
    the dilation portion and the restriction portion are configured to move relative to each other in the insertion direction.

5. The urethral stricture treatment apparatus according to claim 1, wherein
    the restriction portion is configured to be deformed by dilation.

6. The urethral stricture treatment apparatus according to claim 5, wherein
    the restriction portion is a balloon.

7. A urethral stricture treatment method for treating urethral stricture, the urethral stricture treatment method comprising:
inserting a urethral stricture treatment apparatus, which includes a dilation portion that dilates in a state of holding a medical material providing an epithelial function, and a restriction portion that is disposed in a position closer to a distal side than the dilation portion and restricts the movement of the medical material toward the distal side in an insertion direction, into urethra, and wherein the dilation portion and the restriction portion are configured to move relative to each other in the insertion direction;
bringing the restriction portion into contact with external urethral sphincter in a living body;
adjusting a distance between the dilation portion and the restriction portion; and
bringing the medical material into contact with a treatment site by dilating the dilation portion.

8. The urethral stricture treatment method according to claim 7, comprising:
adjusting the distance between the dilation portion and the restriction portion by moving the restriction portion relative to the dilation portion.

9. The urethral stricture treatment method according to claim 7, comprising:
adjusting the distance between the dilation portion and the restriction portion by moving the dilation portion relative to the restriction portion, in a state in which the restriction portion comes into contact with the external urethral sphincter.

10. The urethral stricture treatment method according to claim 7, comprising:
fixing the dilation portion and the restriction portion to a flexible main body portion and which is insertable into the urethra; and
restricting the movement of the medical material toward a proximal side in the insertion direction with a distal side restriction portion which is in a position closer to the distal side than the restriction portion within the main body portion and comes into contact with internal urethral sphincter in the living body.

11. The urethral stricture treatment method according to claim 10, wherein
the main body portion is a transparent or a semitransparent member, and
inserting an endoscope into an insertion lumen inside the main body portion.

12. The urethral stricture treatment method according to claim 7, wherein
the dilation portion has a holding member including a holding portion that is configured to hold the restriction portion, and
the restriction portion is a cyclic member, which is fixed by being held in the holding portion.

13. The urethral stricture treatment method according to claim 10, comprising:
a fixing member with the restriction portion in the outer circumferential portion of the fixing member; and
a fixing balloon which is arranged in the inner circumferential portion of the fixing member and dilates in a circumferential direction so as to fix the fixing member and the main body portion.

14. The urethral stricture treatment method according to claim 7, wherein
the restriction portion is configured to be deformed by dilation.

15. The urethral stricture treatment method according to claim 14, wherein
the restriction portion is a balloon.

* * * * *